US010468130B1

(12) United States Patent
Taneja (10) Patent No.: US 10,468,130 B1
(45) Date of Patent: Nov. 5, 2019

(54) SYSTEM AND METHOD FOR AUTOMATICALLY GENERATING A PRESCRIPTION REFILL ORDER VIA A REPLY ELECTRONIC MESSAGE

(71) Applicant: WALGREEN CO., Deerfield, IL (US)

(72) Inventor: Anshuman Taneja, Vernon Hills, IL (US)

(73) Assignee: WALGREEN CO., Deerfield, IL (US)

( * ) Notice: Subject to any disclaimer, the term of this patent is extended or adjusted under 35 U.S.C. 154(b) by 0 days.

(21) Appl. No.: 16/254,094

(22) Filed: Jan. 22, 2019

Related U.S. Application Data

(63) Continuation of application No. 13/738,556, filed on Jan. 10, 2013, now Pat. No. 10,210,311.

(51) Int. Cl.
*G16H 20/10* (2018.01)
*G06F 19/00* (2018.01)

(52) U.S. Cl.
CPC .................. *G16H 20/10* (2018.01)

(58) Field of Classification Search
None
See application file for complete search history.

(56) References Cited

U.S. PATENT DOCUMENTS

| 5,970,462 | A | * | 10/1999 | Reichert | G06F 19/3456 |
| | | | | | 705/2 |
| 2004/0243588 | A1 | * | 12/2004 | Tanner | G06F 16/2471 |
| 2011/0307265 | A1 | * | 12/2011 | Bannis | G06Q 50/22 |
| | | | | | 705/2 |
| 2013/0218595 | A1 | * | 8/2013 | Burkett | G06Q 40/00 |
| | | | | | 705/3 |

OTHER PUBLICATIONS

Office Action for U.S. Appl. No. 13/738,556, dated Feb. 26, 2016.
Office Action for U.S. Appl. No. 13/738,556, dated Nov. 19, 2015.
Office Action for U.S. Appl. No. 13/738,556, dated May 5, 2015.
Office Action for U.S. Appl. No. 13/738,556, dated Oct. 24, 2014.

* cited by examiner

*Primary Examiner* — Michael Tomaszewski
(74) *Attorney, Agent, or Firm* — Marshall, Gerstein & Borun LLP; Randall G. Reuth (57) ABSTRACT

The method and system may provide a service that allows a customer to order refills of one or more prescription medications in a quick and hassle-free manner from a remote location using a computer or mobile device. The customer replies to an electronic refill reminder that includes refill-eligible prescription numbers and a refill reminder identifier. The system receives the refill reply from the customer and validates the refill reminder identifier. The system then generates a refill order number associated with the refill reminder identifier, retrieves one or more prescription numbers associated with the refill reminder identifier, and transmits the generated refill order number and retrieved one or more prescription numbers for fulfillment. The customer receives a refill order confirmation electronic message from the system.

20 Claims, 7 Drawing Sheets

SYSTEM AND METHOD FOR AUTOMATICALLY GENERATING A PRESCRIPTION REFILL ORDER VIA A REPLY ELECTRONIC MESSAGE

CROSS-REFERENCE TO RELATED APPLICATIONS

This application is a continuation of and claims priority to U.S. application Ser. No. 13/738,556, filed on Jan. 10, 2013, entitled "System and Method for Automatically Generating a Prescription Refill Order via a Reply Electronic Message," the entire contents of which are hereby expressly incorporated by reference.

TECHNICAL FIELD

The present disclosure generally relates to a system and method for refilling prescription medications and, more particularly, to an electronic message reply refill method and system allowing a customer to order one or more prescription refills via a reply electronic message, in an expeditious manner, and preferably without entering login information typically required of online systems.

BACKGROUND

While some medications prescribed to patients may be taken only for a brief period of time, other medications may be taken for extended periods of time. For convenience, when a doctor prescribes a medication that will be taken over an extended period, the doctor may write the prescription such that a pharmacy can refill the prescription one or more times without requiring renewed authorization from the doctor (i.e., without requiring a new prescription). When a patient runs out of the prescribed medication (or slightly before), the patient may contact the pharmacy at which the prescription was originally filled and request a refill, if there are any refills remaining. Of course, if no refills remain, a pharmacist at the pharmacy may contact the doctor to request a new prescription for the same medication without involving the patient.

In the past, a patient (or customer) wishing to order a refill of a prescription medication telephoned the pharmacy or visited the pharmacy to ask for the prescription refill order in person. In some instances, a patient could request a refill of a prescription medication by mail or by facsimile. More recently, pharmacies have implemented internet-based interfaces (i.e., web sites) through which a patient could request a refill. To access the web pages through which prescription refills may be requested, a patient must be logged into a user profile. Generally, though not always, the user profile is associated with only one person, and the user can order refills only of the prescriptions associated with his profile. Some systems allow for a profile to be associated with multiple people (e.g., family members, patients in the charge of a caregiver, etc.), but this requires additional configuration steps that must be performed in advance, such as sending and responding to requests for permission, that often must be coordinated between multiple people.

In any event, the systems currently in place require a user who wishes to order a prescription refill to log into the system. This logging in technique requires the patient to input a user name or an email address and a password. For some patients, remembering the user name or password may be difficult and, if the patient does not have access to the information, the login requirement may prevent access to the system entirely. Even in cases where the patient knows (or has access to) the user name and password, entering the log-in information may be an impediment, especially for users attempting to order refills through a mobile device, many of which have input mechanisms that are difficult or, at least, inconvenient to use. Further, logging into the system requires access to a web browser, which may not be readily available to the customer.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment of thereof. Further, wherever possible, the following description refers to the reference numerals included in the following figures, in which features depicted in multiple figures are designated with consistent reference numerals.

DETAILED DESCRIPTION

Figure 1A:
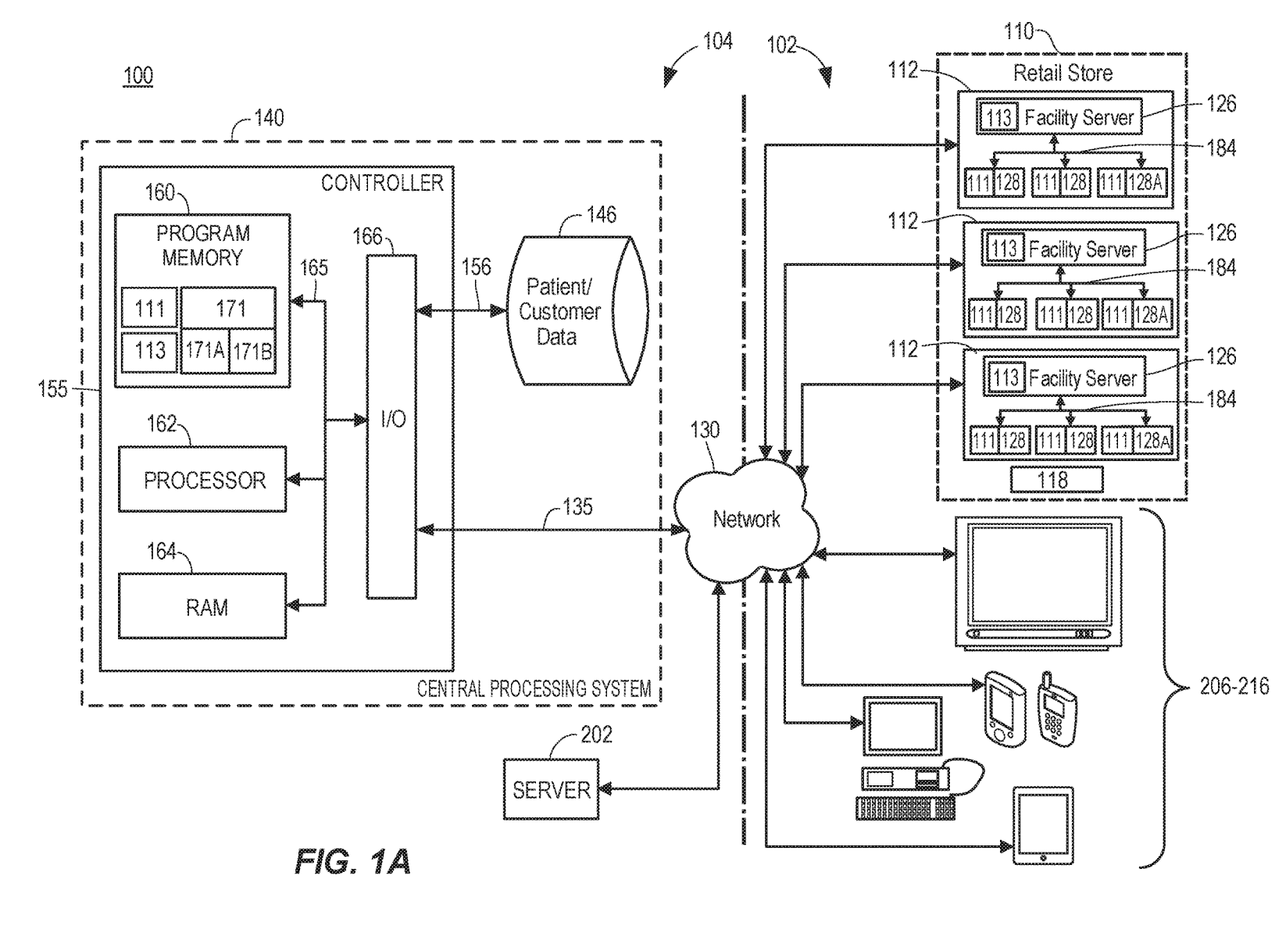
FIG. 1A illustrates a block diagram of a computer network and system on which an exemplary electronic message reply refill system and method may operate in accordance with the described embodiments.

FIG. 1A illustrates various aspects of an exemplary architecture implementing an electronic message reply refill system 100. In particular, FIG. 1A illustrates a block diagram of the exemplary electronic message reply refill system 100. The high-level architecture includes both hardware and software applications, as well as various data communications channels for communicating data between the various hardware and software components. The electronic message reply refill system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists, technicians, and other pharmacy personnel, referred to collectively herein simply as "pharmacists" (not shown), use the pharmacy workstations 128 to access customer information, enter new prescriptions, access insurance and payment information and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. The retail network 110 may also include one or more warehouses or central-filling facilities 118. The warehouses or central-filling facilities 118 may distribute medications or retail products to the various retail pharmacies 112 in the retail network 110, or may distribute medications or retail products directly to customers. Internet-enabled devices 206-216 (e.g., personal computers, cellular phones, smart phones, internet-enabled televisions, etc.) may be communicatively connected to the pharmacies 112 and to a system 140 through a digital network 130, as described below.

Those of ordinary skill in the art will recognize that the front-end components 102 could also comprise a plurality of facility servers 126 disposed at the plurality of pharmacies 112 instead of, or in addition to, a plurality of pharmacy workstations 128. Each of the pharmacies 112 may include one or more facility servers 126 that may facilitate communications between the workstations 128 of the pharmacies 112 via a digital network 130, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126, and vice versa. Moreover, environments other than the pharmacies 112 may employ the workstations 128 and the servers 126. As used herein, the term "pharmacy" refers to any of these environments (e.g., call centers, kiosks, Internet interface terminals, etc.) in addition to the retail pharmacies 112, etc. described above.

The front-end components 102 communicate with the back-end components 104 via the digital network 130. One or more of the front-end components 102 may be excluded from communication with the back-end components 104 by configuration or by limiting access due to security concerns. For example, the internet-enabled devices 206-216 may be excluded from direct access to the back-end components 104. In some embodiments, the pharmacies 112 may communicate with the back-end components via the digital network 130. In other embodiments, the pharmacies 112 and internet-enabled devices 206-216 may communicate with the back-end components 104 via the same digital network 130, but digital access rights, IP masking, and other network configurations may deny access to the internet-enabled devices 206-216.

The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. In addition to one or more servers 202 (described below), the back-end components 104 include the central processing system 140 within a central processing facility, such as, for example, the central processing facility described in U.S. patent application Ser. No. 12/271,686 entitled "DISTRIBUTED PHARMACY PRESCRIPTION PROCESSING SYSTEM" the entire disclosure of which is incorporated by reference herein. Of course, the pharmacies 112 may be communicatively connected to different back-end components 104 having one or more functions or capabilities that are similar to the central processing system 140. The central processing system 140 may include one or more computer processors 162 adapted and configured to execute various software applications and components of the electronic message reply refill system 100, in addition to other software applications. The central processing system 140 further includes a database 146. The database 146 is adapted to store data related to the operation of the electronic message reply refill system 100 (e.g., patient profile data including diagnoses, past healthcare product and medication purchases, prescription histories, etc.) The central processing system 140 may access data stored in the database 146 when executing various functions and tasks associated with the operation of the electronic message reply refill system 100.

Although FIG. 1A depicts the electronic message reply refill system 100 as including the central processing system 140 in communication with three pharmacies 112, and various internet-enabled devices 206-216 it should be understood that different numbers of processing systems, pharmacies, and devices may be utilized. For example, the digital network 130 (or other digital networks, not shown) may interconnect the central processing system 140 to a plurality of included central processing systems 140, hundreds of pharmacies 112, and thousands of internet-enabled devices 206-216. According to the disclosed example, this configuration may provide several advantages, such as, for example, enabling near real-time uploads and downloads of information as well as periodic uploads and downloads of information. This provides for a primary backup of all the information generated in the electronic message reply refill process. Alternatively, some of the pharmacies 112 may store data locally on the facility server 126 and/or the workstations 128.

FIG. 1A also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner.

The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

The program memory 160 may also contain machine-readable instructions (i.e., software) 171, for execution by the processor 162. The software 171 may perform the various tasks associated with operation of the pharmacy or pharmacies, and may be a single module 171 or a plurality of modules 171A, 171B. While the software 171 is depicted in FIG. 1A as including two modules, 171A and 171B, the software 171 may include any number of modules accomplishing tasks related to pharmacy operation including, for example, receiving prescription orders, managing prescription workflow, etc. The central processing system 140 implements a server application 113 for providing data to a user interface application 111 operating on the workstations 128.

Figure 1B:
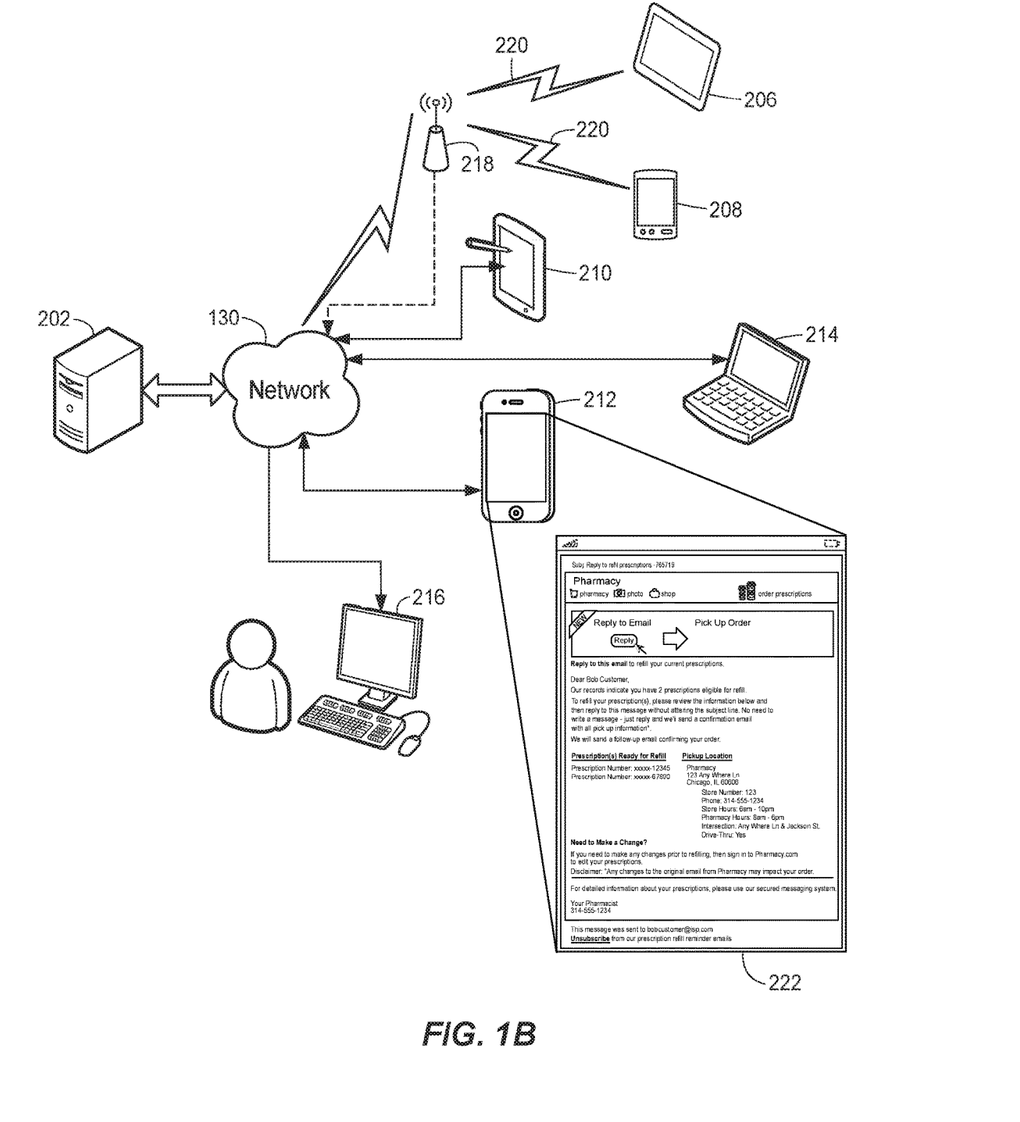
FIG. 1B illustrates internet-enabled devices and associated equipment that may operate with a network and a server.

For purposes of implementing the electronic message reply refill system 100, the user interacts with the server 202 and the pharmacy systems (e.g., the central processing system 140) via an internet-enabled device 206-216 (e.g., mobile device application, web browser application, etc.), a specialized application, or a plurality of web pages. FIG. 1B depicts the server 202 connected via the network 130 to the internet-enabled devices 206-216 through which a user may initiate and interact with the electronic message reply refill system 100 (as shown in FIG. 1A). The internet-enabled devices 206-216 may include, by way of example, a tablet computer 206, an internet-enabled cell phone 208, a personal digital assistant (PDA) 210, a mobile device smartphone 212 also referred to herein as a "mobile device," a laptop computer 214, a desktop computer 216, a portable media player (not shown), etc. Of course, any internet-enabled device appropriately configured may interact with the electronic message reply refill system 100. The internet-enabled devices 206-216 need not necessarily communicate with the network 130 via a wired connection. In some instances, the internet-enabled devices 206-216 may communicate with the network 130 via wireless signals 220 and, in some instances, may communicate with the network 130 via an intervening wireless or wired device 218, which may be a wireless router, a wireless repeater, a base transceiver station of a mobile telephony provider, etc. Each of the internet-enabled devices 206-216 may interact with the server 202 to receive web pages or server data from the server 202 and may display the web pages or server data via a client application (described below). For example, the mobile device 212 may display an email viewing screen 222 of the client application to user, may receive an input from the user, and may interact with the server 202 depending on the type of user-specified input. It will be appreciated that although only one server 202 is depicted in FIG. 1B, multiple servers 202 may be provided for the purpose of distributing server load, serving different web pages, implementing different portions of the pharmacy web interface, etc. These multiple servers 202 may include a web server, an entity-specific server (e.g. an Apple® server, etc.), a server that is disposed in a retail or proprietary network, an independent third-party server that is not under the control of the entity, etc.

Figure 1C:
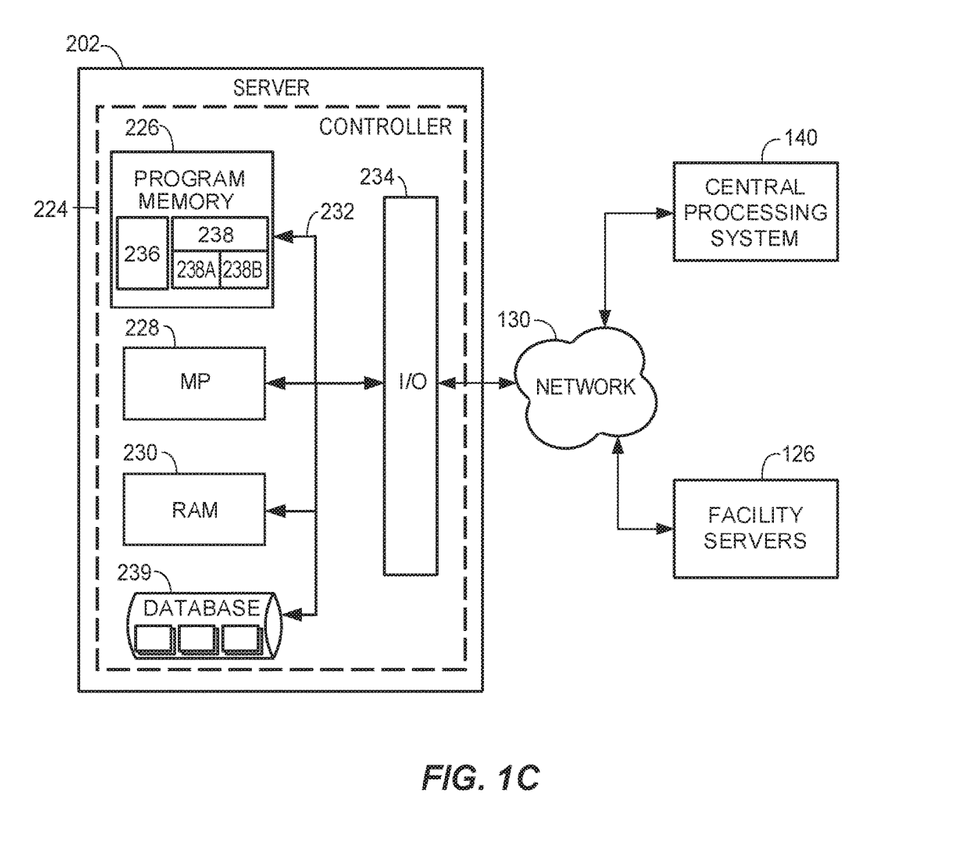
FIG. 1C illustrates a block diagram of an exemplary server.

Turning now to FIG. 1C, the server 202, like the facility server 126, includes a controller 224. Similar to the controllers 155 and 170, the controller 224 includes a program memory 226, a microcontroller or a microprocessor (MP) 228, a random-access memory (RAM) 230, and an input/output (I/O) circuit 234, all of which are interconnected via an address/data bus 232. In some embodiments, the controller 224 may also include, or otherwise be communicatively connected to, a database 239 or other data storage mechanism (e.g., one or more hard disk drives, optical storage drives, solid state storage devices, etc.). The database 239 may include data such as customer web profiles, product data, mobile device application data, web page templates and/or web pages, an email inbox (not shown) that stores and indexes received and sent emails, and other data necessary to interact with the user through the network 130. As discussed with reference to the controllers 155 and 170, it should be appreciated that although FIG. 1C depicts only one microprocessor 228, the controller 224 may include multiple microprocessors 228. Similarly, the memory of the controller 224 may include multiple RAMs 230 and multiple program memories 226. Although the FIG. 1C depicts the I/O circuit 234 as a single block, the I/O circuit 234 may include a number of different types of I/O circuits. The controller 224 may implement the RAM(s) 230 and the program memories 226 as semiconductor memories, magnetically readable memories, and/or optically readable memories, for example.

In addition to being connected through the network 130 to the internet-enabled devices 206-216, as depicted in FIG. 1B, FIG. 1C illustrates that the server 202 may also be connected through the network 130 to the central processing system 140 and/or one or more facility servers 126. As described below, the connection of the server 202 to the central processing system 140 assists in facilitating some of the functionality of the electronic message reply refill process. As a result, the server 202 may act as a routing or interfacing server between the plurality of internet-enabled devices 206-216 and a destination server, namely, the central processing system 140. For example, the server 202 may be configured to communicate the central processing system 140 and with the internet-enabled device 206-216 via a multitude of protocols, such as packet-switched protocols, web services, web APIs, etc. The server 202 may also convert (if necessary) and route client application data (not shown) to the appropriate server, such as the central process system 140 for example. Additionally, the server 202 may act as the destination server and need not route any data from the internet-enabled device 206-216.

As shown in FIG. 1C, the program memory 226 and/or the RAM 230 may store various applications for execution by the microprocessor 228. For example, a user-interface application 236 may provide a user interface to the server 202, which user interface may, for example, allow a network administrator to configure, troubleshoot, or test various aspects of the server's operation, or otherwise to access information thereon. A server application 238 operates to populate and transmit client application data and web pages to the internet-enabled devices 206-216, receive information from the user transmitted back to the server 202, and forward appropriate data to the central processing system 140 and the facility servers 126, as described below. Like the software 171 of FIGS. 1A and 1B, the server application 238 may be a single module 238 or a plurality of modules 238A, 238B. While the server application 238 is depicted in FIG. 1C as including two modules, 238A and 238B, the server application 238 may include any number of modules accomplishing tasks related to implantation of the server 202. By way of example, the module 238A may populate and transmit the client application data and/or may receive and evaluate inputs from the user to receive a data access request, while the module 238B may communicate with one or more of the back end components 104 to fulfill a data access request.

Figure 1D:
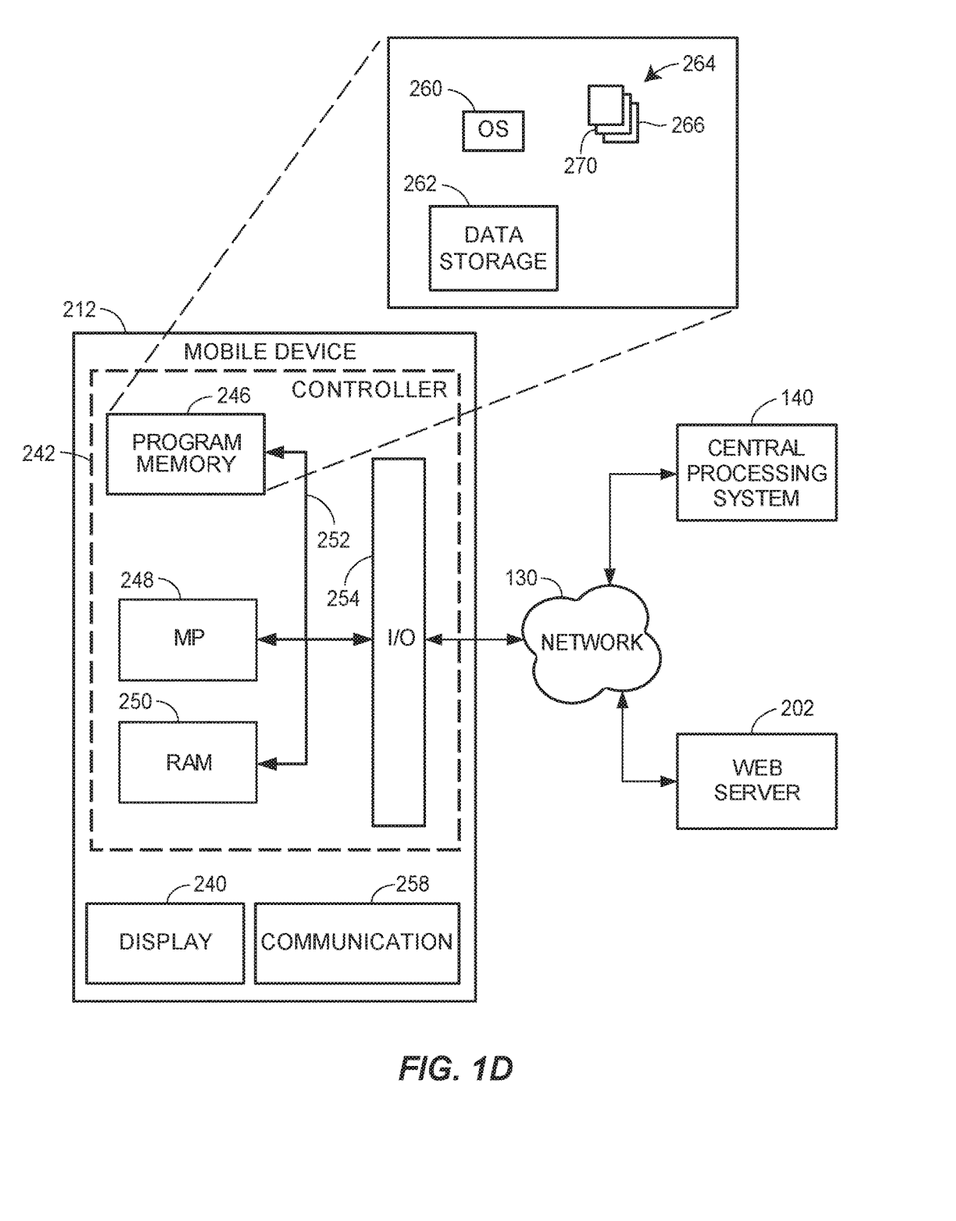
FIG. 1D illustrates a block diagram of an exemplary mobile device.

Referring now to FIG. 1D, the mobile device 212 (or any of the internet-enabled devices 206-216) includes a display 240, a communication unit 258, a user-input device (not shown), and, like the server 202, a controller 242. Similar to the controllers 155 and 224, the controller 242 includes a program memory 246, one or more microcontroller or a microprocessor (MP) 248, a random-access memory (RAM) 250, and an input/output (I/O) circuit 254, all of which are interconnected via an address/data bus 252. The program memory 246 includes an operating system 260, a data storage 262, and a plurality of software applications 264. The operating system 260, for example, may include one of a plurality of mobile platforms such as the iOS®, Android™, Palm® webOS, Windows Mobile/Phone, Black- Berry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage 262 may include data such as user profiles, application data for the plurality of applications 264, and other data necessary to interact with the server 202, the facility servers 126, or the server applications 113 through the digital network 130. In some embodiments, the controller 242 may also include, or otherwise be communicatively connected to, other data storage mechanisms (e.g., one or more hard disk drives, optical storage drives, solid state storage devices, etc.) that reside within the mobile device 212.

The communication unit 258 may communicate with the server 202 via any suitable wireless communication protocol network, such as a wireless telephony network (e.g., GSM, CDMA, LTE, etc.), a wi-fi network (802.11 standards), a WiMAX network, a Bluetooth network, etc. The user-input device (not shown) may include a "soft" keyboard that is displayed on the display 240 of the mobile device 212, an external hardware keyboard communicating via a wired or a wireless connection (e.g., a Bluetooth keyboard), an external mouse, or any other suitable user-input device. As discussed with reference to the controllers 155 and 224, it should be appreciated that although FIG. 1D depicts only one microprocessor 248, the controller 242 may include multiple microprocessors 248. Similarly, the memory of the controller 242 may include multiple RAMs 250 and multiple program memories 246. Although the FIG. 1D depicts the I/O circuit 254 as a single block, the I/O circuit 254 may include a number of different types of I/O circuits. The controller 242 may implement the RAM(s) 250 and the program memories 246 as semiconductor memories, magnetically readable memories, and/or optically readable memories, for example.

The one or more processors 248 may be adapted and configured to execute any one or more of the plurality of software applications 264 residing in the program memory 242, in addition to other software applications. One of the plurality of applications 264 may be a mail client application 266 that may be implemented as a series of machine-readable instructions for performing the various tasks associated with receiving information at, displaying information on, and transmitting information from the mobile device 212. The mail client application 266 may store an email inbox (not shown) in the data storage 262 that stores and indexes received and sent emails. One of the plurality of applications 264 may be a native web browser 270, such as Apple's Safari®, Google Android™ mobile web browser, Microsoft Internet Explorer® for Mobile, Opera Mobile™, that may be implemented as a series of machine-readable instructions for receiving, interpreting, and displaying web page information from the server 202, the facility servers 126, or the server applications 113 while also receiving inputs from the user.

Preferably, a customer, a patient, or a user may launch the mail client application 266 from an internet-enabled device, such as one of the internet-enabled devices 206-216, to access the server 202 cooperating with the central processing system 140 and the pharmacies 110 to implement the electronic message reply refill system 100. Additionally, the customer, the patient, or the user may also launch or instantiate any other suitable user interface application (e.g., the native web browser 270, or any other one of the plurality of software applications 264) to access the server 202, the facility servers 126, or the server applications 113 to realize the electronic message reply refill system 100. As used herein, the term "customer" indicates someone purchasing a retail product but may additionally be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason or desire to purchase one or more retail products or to perform one or more functions relating to prescription medications, whether the prescriptions are related to a single patient or multiple patients. For example, a customer could be a caregiver responsible for patients with a specific disease that progresses in a known manner. The caregiver customer might greatly benefit from gaining information related to various medications and health products to assist in his or her caregiver responsibilities. In any event, while the term "customer" may be used interchangeably with the term "patient," in this specification the term "customer" is used primarily so as to avoid confusion. Generally, the term "user" is used when referring to a person who is operating one of the internet-enabled devices 206-216 and is not exclusive of the terms "customer" and "patient."

As described above, one or both of the databases 146 and 239, illustrated in FIGS. 1A and 1B, respectively, include various information about the pharmacy's customers and the prescriptions filled by the pharmacy, as well as basic biographical information about the customer, such as a customer name, a customer identifier (e.g., an email address of the customer, etc.), a customer address, a customer phone number, an insurance carrier associated with the customer, an insurance group number for the customer, an insurance ID number for the customer, a customer birth date, a health history or condition, customer purchase history, etc.

The purchase history may include data related to purchases the customer routinely makes or has made at the pharmacies 110. The purchase history data may include any product sold by the pharmacies 110 and purchased by a customer, whether in person or online. Where purchases are made by the customer in the store, the purchase data made be linked to the customer record though credit card, an in-store savings card, or other type of point-of-sale identification. Where the purchases are made by the customer over the network 130 or online, the purchases may be linked to the customer record through a web-based profile that is accessible by the customer through the web-enabled device 206-216, as herein described. Additionally, the customer profile may include other information such as credit card information or other payment information, one or more customer email addresses, user name and/or password information, online security question/answer information, etc. Of course, the customer record may also include other, more or less information than that described above.

Customer records, including a customer's prescription order records, are among the exemplary data that the electronic message reply refill system 100 may store on the databases 146 and 239. The customer record also includes prescription data for each prescription filled by the pharmacy for the customer. The prescription data generally include, but are not limited to: a name of the medication; an indication whether a generic may be substituted; a dose (i.e., pills per day) of the medication; a number of days of medication to be dispensed (also referred to herein as a "day supply" or a "prescribed day supply"); a number of refills prescribed; a number of refills remaining; a prescription date; a prescribing physician; a phone number for the prescribing physician; a date on which the prescription was most recently adjudicated; a calculated date on which the prescription may next be adjudicated for the prescription; a remaining day supply for the prescription; a percent-consumption period indicating the number of days it would take to consume the required minimum percent-fill consumed of the fill for the prescription); and a prescription number. Of course, the prescription data need not include all of the information above, such as when the electronic message reply refill system 100 determines some information (e.g., the next adjudication date) but does not store it, or stores it some place other than with the prescription data in the database 146 or the database 239. Moreover, the prescription data may include additional information not mentioned above.

In any event, the electronic message reply refill system 100 may perform various tasks, such as sending an electronic message refill reminder (e.g., an email, a text, an instant message, etc.) that includes one or more refill-eligible prescriptions to a customer when the customer's one or more prescriptions are eligible for refill. In response to receiving the electronic message refill reminder, the customer may place a refill order for one or more refill-eligible prescriptions by solely replying to the received electronic message refill reminder.

In generating the electronic message refill reminder, for example, the server 202 or the central processing system 140 may query the databases 146 and 239 to obtain prescription data from the customer records to determine, for a given customer, whether one or more prescriptions are eligible (or soon to be eligible) for refill. For each prescription, the system 100 may use any type of stored prescription data, such as the number of refills remaining, the remaining day supply for the prescription, order records, etc., from the customer records to determine whether a particular prescription is eligible for refill. After this determination, the system 100 may group the refill-eligible prescriptions together on a per customer (or per customer family, etc.) basis to more efficiently remind the customer that multiple prescriptions are eligible for refill. Additionally, the system 100 may generate and assign a refill reminder identifier (described below) to the one or more refill-eligible prescriptions and also associated the refill reminder identifier with the customer identifier, such as the customer's email address. The system 100 may then store the newly generated refill reminder identifier within a database of refill reminder identifiers (e.g., one of the databases 140, 239). In generating a refill reminder email (described below), for example, the system 100 preferably may insert the newly assigned refill reminder identifier into the subject line of the refill reminder email so that when the customer replies the to refill reminder email, the refill reminder identifier will be easily extracted by the system 100 parsing the text of the subject line. Furthermore, the system 100 may also include the customer's biographical information, the prescription numbers preferably masked for privacy reasons, the pharmacy (and the information of the pharmacy) associated with the one or more refill-eligible prescriptions (e.g., the pharmacy location where the one or more prescriptions were last filled, etc.), or any other desired information in the refill reminder email. The server 202 may send, using the customer's email address, this newly generated refill reminder email to the customer to alert the customer that one or more prescriptions are eligible for refill.

As shown in FIG. 1B, to access the server 202, the facility servers 126, or the server applications 113, the user may execute the mail client application 266 or the web browser 270 on one of the internet-enabled devices 206-216, such as the mobile device 212. Using the mail client application 266, for instance, the user may request to view any emails, such as the refill reminder email described above, or other electronic messages transmitted by the server 202 to the mobile device 212. In any event, the user may launch the mail client application 266 from one of the internet-enabled devices 206-216 via any suitable manner, such as touch-selecting a mail client application icon (not shown) on the display 240 of the mobile device 212, double-clicking on the mail client application icon via a mouse of a computer 216 or a trackpad (not shown) of a laptop 214. After the user launches the mail client application 266, an inbox screen (not shown) of the mail client application 266 is displayed to the user on the mobile device 212. The user may navigate and may select a particular email message, such as a refill reminder email (described below), within the inbox from the server 202.

Figure 2:
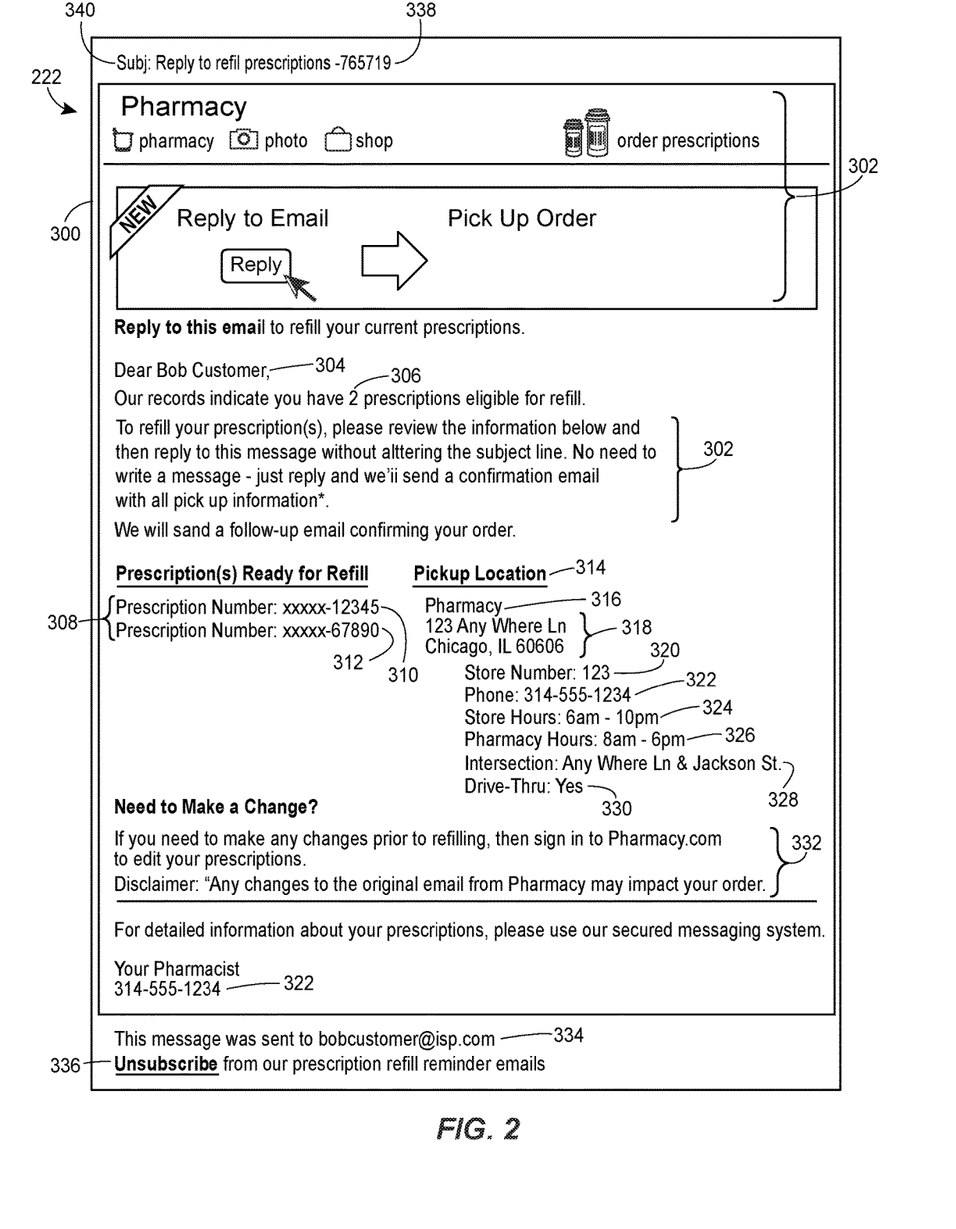
FIG. 2 depicts a exemplary refill reminder email transmitted by the server of FIG. 1C.

With reference now to FIG. 2, a refill reminder email 300, as shown in the an email viewing screen 222 of the mail client application 266, for example, is displayed to a user on a client device, such as the mobile device 212, a smartphone, a tablet, a laptop, or any other internet-enabled device 206-216. The refill reminder email 222 of the mail client application 266 may be stand alone or displayed within the native web browser 270. The refill reminder email 300 may include a banner 302 that conveys the pharmacy's name, the types of services the pharmacy offers, directions in using the electronic message reply refill system 100, advertisements, etc. Moreover, the refill reminder email 300 may include a name of the customer 304, a number count of prescriptions 306 associated with the customer that are eligible for refill, and a listing of the prescription numbers 308. Each individual prescription number 310, 312 in the listing of the prescription numbers 308 corresponds to a particular prescription medication associated with the customer that is eligible for refill. Each prescription number 310, 312 may be masked or partially hidden to protect the privacy of the customer in case the email is incorrectly sent to someone other than the customer. For example, the prescription number 310 is labeled as "XXXXX-12345" in FIG. 2 so that only the last five digits are exposed and the first five digits remain undisclosed. However, the customer may still identify and verify each prescription number 310, 312 via the last five digits.

As illustrated in FIG. 2, the refill reminder email 300 may also include a pickup location 314 where the customer may physically retrieve her refilled prescriptions. Generally, the pickup location 314 is the pharmacy where the customer last picked up her prescriptions, but of course the pickup location may include any pharmacy that is determined in any manner. The pickup location 314, for example, may include a pharmacy name 316, a pharmacy address 318, a pharmacy phone number 320, store hours for the pharmacy 324, pharmacy hours for the pharmacy 326, a nearby intersection to the location of the pharmacy 328, and an indicator 330 of whether the pharmacy includes a drive through. The refill reminder email 300 may include instructions 332 that allow the customer to edit any of the prescription information or pickup location information if the information is incorrect. For example, the instructions 332 may include a hyperlink that, in response to being selected, directs the customer to a log in web page (not shown) that allows the customer to interact with the system 100 to edit any incorrect information. The refill reminder email 300 may also include an identity notification 334 that allows the customer to verify that the refill reminder email 300 is intended for the customer via the email of the customer for example. Moreover, if the customer desires to no longer receive refill reminder emails 300 from the electronic message refill reply system 100, the customer may select an unsubscribe link 336 to opt out of the refill reminder email service.

Importantly, a subject line 340 of the refill reminder email 300 includes a refill reminder identifier 338 that associates the listing of the prescription numbers 308 and the customer's email address 334. For example, in FIG. 2, the refill reminder identifier 338 appears in the subject line 340 as "765719" and is used by the electronic message refill reply system 100 to assist in tracking the refill transactions or orders associated with the customer and the refill-eligible prescriptions 310, 312 of the listing of prescription numbers 308.

In any event, after receiving the refill reminder email 300, the customer may review and verify the email address 334, the listing of prescription numbers 308, the pharmacy information 316-330 associated with the pickup location 314 within the refill reminder email 300. When the customer is satisfied that the above information is correct and desires to place a refill order for the listing of prescriptions 308, the customer may select a reply selector (not shown) within the mail client application 266 or within the web browser 270 to respond to the refill reminder email 300. By selecting the reply selector (not shown), the mail client application 266 or web browser 270 generates a reply electronic message (not shown) addressed to a reply email address that preferably identifies the server 202. Advantageously, the newly generated reply electronic message includes the entire content of the subject line 340 of the received refill reminder electronic message (including the refill reminder identifier in addition to the indicator "Re:" that signifies that the email is a reply electronic message. For example, the subject line 340 of the received refill reminder email 300 recites "Reply to refill prescriptions—765719". When the customer replies to the refill reminder email 300, the newly generated reply email recites "Re: Reply to refill prescriptions—765719" and allows the server 202 to authenticate and to process the incoming reply email for refill at the appropriate pharmacy.

Figure 3:
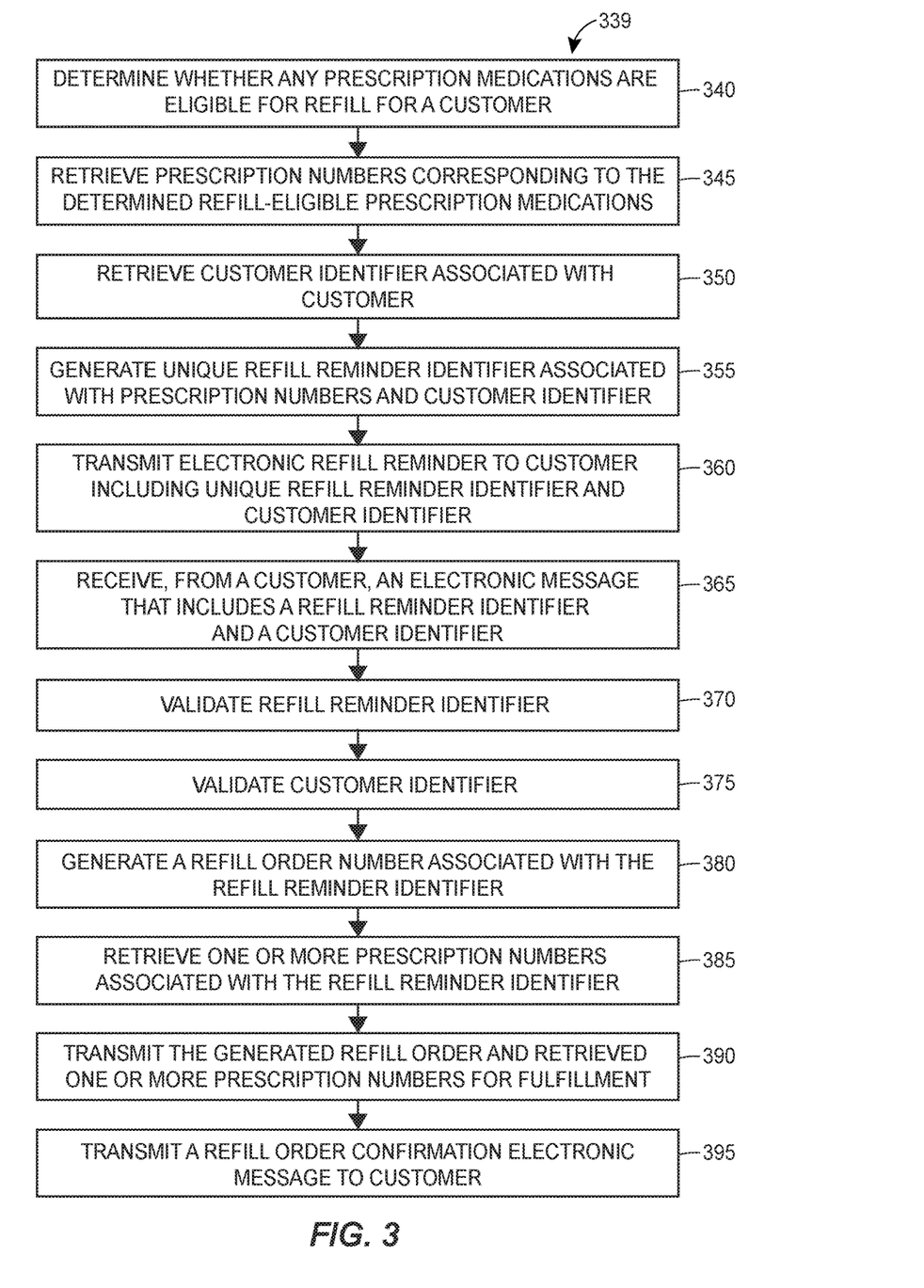
FIG. 3 illustrates an exemplary method implementing the electronic message reply refill system in accordance with the presently described embodiments.

FIG. 3 depicts an overview 339 of an electronic message reply refill method performed by the electronic message reply refill system 100. Generally speaking, the electronic message reply refill method begins by determining whether any prescription medications are eligible for refill for a particular customer (block 340) and then retrieving the one or more prescription numbers (e.g., the prescription numbers 310, 312) corresponding to the determined refill-eligible prescription medications (block 345). After retrieving the customer identifier (e.g., the customer identifier 334) associated with the customer (block 350), the system 100 generates a unique refill reminder identifier (e.g., the refill reminder identifier 338) that is associated with the retrieved one or more prescription numbers and the customer identifier (block 355) and then transmits, from the server 202, an electronic refill reminder (to the internet-enabled device 206-216 of the customer) including the unique refill reminder identifier and the customer identifier (block 360). The system 100 receives from the customer the refill reply electronic message including the unique refill reminder identifier and the customer identifier at the server 202 (block 365). After the system 100 validates the refill reminder identifier by verifying that the unique refill reminder identifier exists in a database of refill reminder identifiers (block 370) and validates the customer identifier by verifying that the customer identifier exists in a database of customer identifiers (block 375), the system 100 generates a refill order number associated with the refill reminder identifier (block 380). The system 100 retrieves one or more prescription numbers associated with the refill reminder identifier from the one or more databases 146 and 239 (block 385). The system 100 transmits the generated refill order number and retrieved one or more prescriptions to the appropriate pharmacy 112 for fulfillment (block 390). Having received order confirmation from the pharmacy, the server 202 may transmit, to the customer, a refill order confirmation electronic message that makes the customer aware of the refill order confirmation (block 395).

Figure 4:
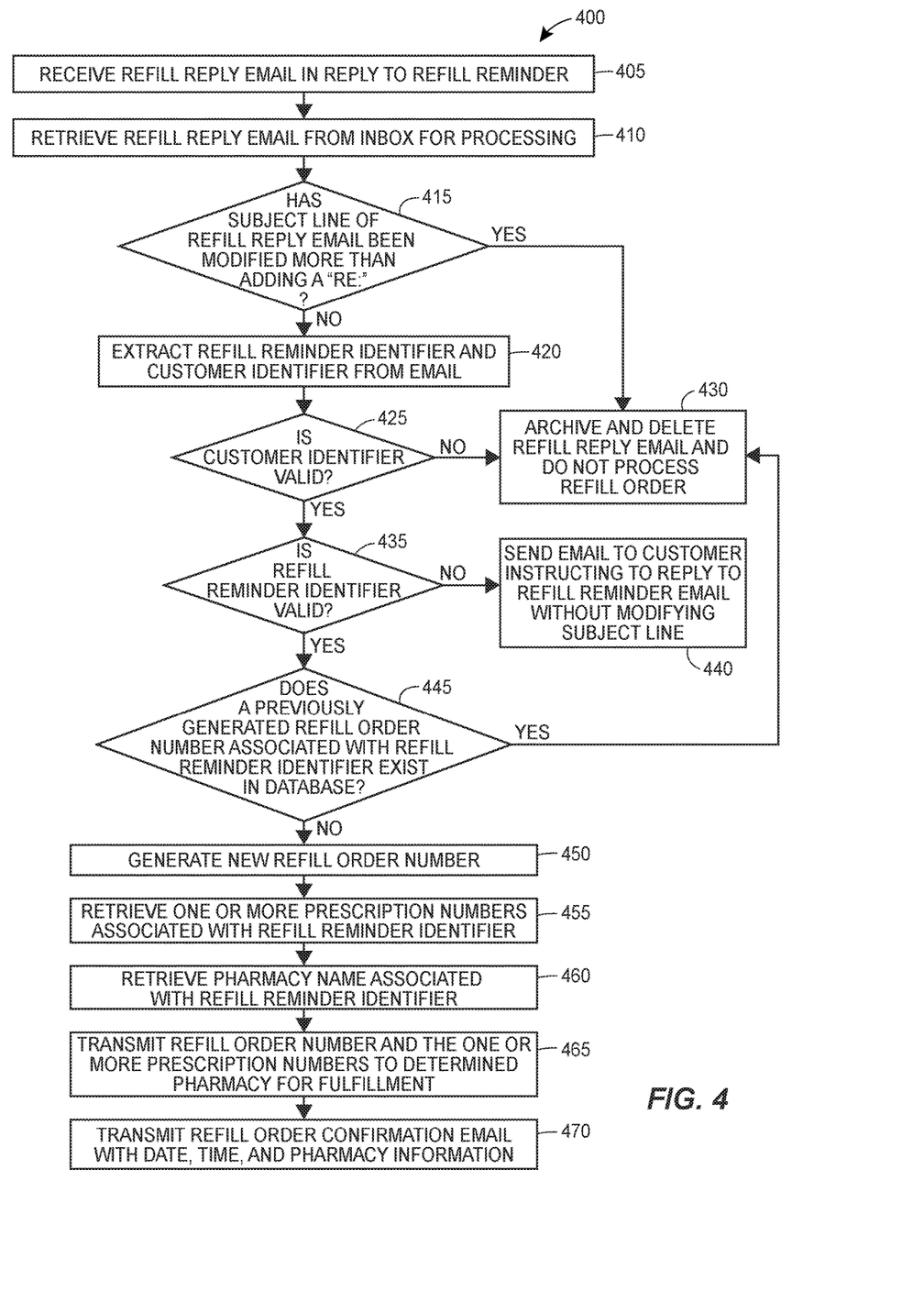
FIG. 4 illustrates an exemplary detailed method implementing the electronic message reply refill system in accordance with the presently described embodiments.

The method 400 illustrated in FIG. 4 provides additional detail about the method executed by the electronic message reply refill system 100. In one of the various manners described above, a customer may enter the electronic message reply refill system 100 by, for example, replying to the refill reminder email 300 via the mail client application 266 or the web browser 270. Of course, the customer could alternatively enter the electronic message reply refill system 100 by replying to a text message or instant message.

In any event, upon receiving a refill reply electronic message, such as an email, that is in reply to a refill reminder email (block 405), the server 202 retrieves the received refill reply email from the email inbox (not shown) stored in the database 239 (block 410). Because the high volume of refill reply emails, the server 202 may also retrieve groups of emails in batches from the inbox at periodic intervals opposed to retrieving each email individually. For example, the server 202 may retrieve a batch of 5,000 emails every ten minutes from the inbox to assist the system 100 in better processing the incoming refill reply emails. Of course, the number of emails retrieved in each batch and the periodic time intervals may be of any amount.

After retrieving the refill reply email from the email inbox, the server 202 may determine whether the text in the subject line 340 has been modified except for an added reply message indicator (e.g., the added term "Re:" in a subject line 340 of an email specifies that the received email is in response to another email) (block 415). The server 202 preferably may be implemented to recognize specific phrases of text while ignoring the phrase "Re:" to assist in determining whether the subject line 340 of the retrieved email has been modified. This initial determination of whether the subject line 340 has been modified may assist in filtering out automatic reply emails (e.g., an "Out of Office" reply email, a "On Vacation" email, etc.) or unsolicited "spam" emails. For example, if the server 202 retrieves an email that includes a term "AutoReply" or a term "Out of Office" that has been added to the subject line 340, one may assume that an automated system automatically sent the email rather than a human sending the email. In any event, if the server 202 determines that an automatic reply email has been sent, the server 202 may archive the email, may delete the email from the inbox, and may not process the refill order (block 430). If server 202 determines that the subject line 340 of the retrieved email has not been modified except for the added reply message indicator, then the server 202 extracts the refill reminder identifier 338 and the customer identifier 334 from the subject line 340 and an email address from a "from" field in the email, respectively (block 420). Of course, the system 100 may use the refill reminder identifier 338 only to identify the prescriptions to be refilled and may omit the use of the customer identifier 334 in its entirety.

After the extraction of the refill reminder identifier 338 and the customer identifier 334, the server 202 may proceed to validate the customer identifier 334 (block 425). Validation of the customer identifier 334 may include one process or multiple steps. In various embodiments, the server 202 may check the length of the customer identifier 334 (e.g., to determine whether it is the correct length), determine whether the customer identifier 334 includes any unacceptable characters (e.g., special characters, non-numeric characters, etc.), and/or determine whether the customer identifier 334 includes a delimiter (e.g., a hyphen or a space). Of course, some embodiments may validate the extracted customer identifier 334 in each of these manners. Validation of the customer identifier 334 may also include validating the customer identifier 334 against a database of customer identifiers (e.g., in one of the databases 146, 239). This validation against a database method is preferable when the email address 334 of the customer is used as the customer identifier 334. In any event, if the electronic message reply refill system 100 determines that the customer identifier 334 is invalid (block 425), the server 202 may archive the reply refill email, may delete the reply refill email, and may not process the refill order (block 430). If, instead, the system 100 determines that the customer identifier 334 is valid, the system 100 proceeds to determine whether the extracted refill reminder identifier 338 is valid (block 435).

Validation of the refill reminder identifier 338 may include similar processes or steps as to the customer identifier 334 validation process described above including checking the length of the refill reminder identifier 338, determining whether the refill reminder identifier 338 includes any unacceptable characters, validating the customer identifier 334 against a database of refill reminder identifiers, and/or determining whether the refill reminder identifier 338 includes a delimiter (e.g., a hyphen or a space). Of course, some embodiments may validate the extracted refill reminder identifier 338 in each of these manners. If the system 100 determines that the refill reminder identifier 338 is invalid (block 435), the server 202 may transmit a new electronic message that instructs the customer to resend a reply to the refill reminder email 300 without modifying the subject line 340 (block 440). The server 202 may then archive the reply refill email, may delete the reply refill email, and may not process the refill order (block 430). However, if the system 100 determines that the refill reminder identifier 338 is valid, the system 100 proceeds to determine whether a previously generated refill order number (not shown) associated with the refill reminder identifier 338 exists in the order number database (e.g., in one of the databases 146, 239) (block 445).

Using the refill reminder identifier 338, the server 202 may determine whether a previously generated refill order number that is associated with the refill reminder identifier 338 exists in a database of refill order numbers. A refill order number is generated at the time of placing a prescription fill order and is associated with a specific refill reminder identifier 338. In querying the database of order numbers for a refill order number that is associated with a specific refill reminder identifier 338, the server 202 may verify the previous placement of a refill order. This verification prevents the server 202 from placing duplicate refill orders because the refill reminder identifier 338 may only be associated with one refill order number. If the system 100 determines that a refill order number exists in the database of order numbers, the server 202 may then not process the already processed order and may archive and then delete the reply refill email (block 430). If, however, the system 100 determines that no related refill order numbers exist in the order number database, the system 100 proceeds to generate a new refill order number that is associated with the refill reminder identifier 338 (block 450).

The server 202 may store the newly generated refill order number and associate the refill order number with the refill reminder identifier 338. Using the refill reminder identifier 338, the system 100 may then retrieve one or more prescription numbers 310, 312 that are associated with the extracted refill reminder identifier 338 from a database of prescription numbers (e.g., in one of the databases 146, 239) (block 455). Additionally, the system 100 may retrieve the pharmacy name 316 associated with the extracted refill reminder identifier 338 from a database of pharmacy information (e.g., in one of the databases 146, 239) (block 460). After determining the pharmacy 112 and one or more prescription numbers associated with the extracted refill reminder identifier 338, the system 100 may transmit the newly generated refill order number and the determined one or more prescription numbers to the determined pharmacy 112 for fulfillment (block 465). The pharmacy 112, in response, may transmit a confirmation that the refill order number and one or more prescription numbers are safely received and that the refill order is placed. In response to receiving this confirmation, the server 202 may transmit a refill order confirmation email to the customer that may include a confirmation that the refill order was placed, a status of the refill order, a date, a time, and pharmacy information (block 470).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

I claim:

1. A method of generating a refill order for one or more prescription medications via a reply electronic message to an electronic refill reminder, the method executed by one or more computer processors programmed to perform the method, the method comprising:

determining whether one or more prescription medications are eligible for refill for a customer;

retrieving one or more prescription numbers corresponding to the one or more determined refill-eligible prescription medications for the customer;

generating a unique refill reminder identifier associated with the one or more retrieved prescription numbers;

transmitting, over a network, an electronic refill reminder to the customer, the electronic refill reminder including at least the generated unique refill reminder identifier;

receiving, over the network, a reply from the customer, the reply being sent in response to the customer receiving the electronic refill reminder;

validating the unique refill reminder identifier by verifying that the unique refill reminder identifier exists in a database of refill reminder identifiers, the refill reminder identifiers corresponding to previously sent electronic refill reminders;

generating a unique refill order number associated with the unique refill reminder identifier;

retrieving, using the unique refill reminder identifier, one or more prescription numbers associated with the unique refill reminder identifier, each prescription number corresponding to a previously filled prescription medication and a patient; and transmitting, over the network, a refill order confirmation electronic message to the customer, the refill order confirmation electronic message including refill order confirmation information for the one or more prescription medications.

2. The method of claim 1, wherein retrieving the one or more prescription numbers corresponding to the one or more determined refill-eligible prescription medications for the customer further includes retrieving a customer identifier associated with the customer, wherein generating the unique refill reminder identifier includes generating the unique refill reminder identifier associated with the one or more retrieved prescription numbers and the retrieved customer identifier, wherein transmitting, over the network, the electronic refill reminder includes transmitting, over the network, the electronic refill reminder to the customer, the electronic refill reminder including at least the generated unique refill reminder identifier and the customer identifier, and further comprising:

validating the customer identifier by verifying that the customer identifier exists in a database of customer identifiers, the customer identifiers corresponding to customers that previously filled at least one prescription medication.

3. The method of claim 2, wherein determining whether one or more prescription medications are eligible for refill for the customer includes determining, using the customer identifier associated with the customer, all prescription medications associated with the customer identifier that are eligible for refill.

4. The method of claim 1, wherein generating the refill order number includes:

verifying whether a previously generated refill order number that is associated with the unique refill reminder identifier exists in a database of refill order numbers corresponding to previously filled orders; and generating the refill order number only if no previously generated refill order number that is associated with the unique refill reminder identifier is found the database of refill order numbers.

5. The method of claim 1, wherein validating the unique refill reminder identifier includes determining whether the unique refill reminder identifier includes a delimiter.

6. The method of claim 5, wherein validating the unique refill reminder identifier includes transmitting, over the network, in response to the unique refill reminder identifier being invalid, an instructional electronic message that instructs the customer to reply to the electronic refill reminder again without modifying the refill reminder identifier.

7. The method of claim 1, wherein transmitting the refill order confirmation electronic message includes transmitting pharmacy information and a status of the refill order.

8. The method of claim 1, wherein the reply includes the unique refill reminder identifier.

9. A non-transitory computer-readable storage medium having stored thereon a set of instructions, executable by a processor, for generating a refill order for one or more prescription medications via a reply electronic message to an electronic refill reminder, the instructions, when executed by the processors, cause the processor to:

determine whether one or more prescription medications are eligible for refill for a customer;

retrieve one or more prescription numbers corresponding to the one or more determined refill-eligible prescription medications for the customer;

generate a unique refill reminder identifier associated with the one or more retrieved prescription numbers;

transmit, over a network, an electronic refill reminder to the customer, the electronic refill reminder including at least the generated unique refill reminder identifier;

receive, over the network, a reply from the customer, the reply being sent in response to the customer receiving the electronic refill reminder;

validate the unique refill reminder identifier by verifying that the unique refill reminder identifier exists in a database of refill reminder identifiers, the refill reminder identifiers corresponding to previously sent electronic refill reminders;

generate a unique refill order number associated with the unique refill reminder identifier;

retrieve, using the unique refill reminder identifier, one or more prescription numbers associated with the unique refill reminder identifier, each prescription number corresponding to a previously filled prescription medication and a patient; and transmit, over the network, a refill order confirmation electronic message to the customer, the refill order confirmation electronic message including refill order confirmation information for the one or more prescription medications.

10. The non-transitory computer-readable storage medium of claim 9, wherein to retrieve the one or more prescription numbers corresponding to the one or more determined refill-eligible prescription medications for the customer, the instructions cause the processor to:

retrieve a customer identifier associated with the customer;

generate the unique refill reminder identifier associated with the one or more retrieved prescription numbers and the retrieved customer identifier;

transmit, over the network, the electronic refill reminder to the customer, the electronic refill reminder including at least the generated unique refill reminder identifier and the customer identifier; and validate the customer identifier by verifying that the customer identifier exists in a database of customer identifiers, the customer identifiers corresponding to customers that previously filled at least one prescription medication.

11. The non-transitory computer-readable storage medium of claim 9, wherein to determine whether one or more prescription medications are eligible for refill for the customer, the instructions cause the processor to determine, using the customer identifier associated with the customer, all prescription medications associated with the customer identifier that are eligible for refill.

12. The non-transitory computer-readable storage medium of claim 9, wherein to generate the refill order number, the instructions cause the processor to:
verify whether a previously generated refill order number that is associated with the unique refill reminder identifier exists in a database of refill order numbers corresponding to previously filled orders; and
generate the refill order number only if no previously generated refill order number that is associated with the unique refill reminder identifier is found the database of refill order numbers.

13. The non-transitory computer-readable storage medium of claim 9, wherein to validate the unique refill reminder identifier, the instructions cause the processor to determine whether the unique refill reminder identifier includes a delimiter.

14. The non-transitory computer-readable storage medium of claim 13, wherein to validate the unique refill reminder identifier, the instructions cause the processor to transmit, over the network, in response to the unique refill reminder identifier being invalid, an instructional electronic message that instructs the customer to reply to the electronic refill reminder again without modifying the refill reminder identifier.

15. The non-transitory computer-readable storage medium of claim 9, wherein the refill order confirmation electronic message includes pharmacy information and a status of the refill order.

16. The non-transitory computer-readable storage medium of claim 11, wherein the reply includes the unique refill reminder identifier.

17. A system for receiving and generating a refill order for one or more prescription medications via an electronic message, the system comprising:
a communication network;
a client device communicatively coupled to the communication network;
a server communicatively coupled to the communication network, the server comprising a non-transitory computer-readable medium storing instructions, executable by a processor in the server to:
determine whether one or more prescription medications are eligible for refill for a customer;
retrieve one or more prescription numbers corresponding to the one or more determined refill-eligible prescription medications for the customer;
generate a unique refill reminder identifier associated with the one or more retrieved prescription numbers;
transmit, over the communication network, an electronic refill reminder to the customer, the electronic refill reminder including at least the generated unique refill reminder identifier;
receive, over the communication network, a reply from the customer, the reply being sent in response to the customer receiving the electronic refill reminder;
validate the unique refill reminder identifier by verifying that the unique refill reminder identifier exists in a database of refill reminder identifiers, the refill reminder identifiers corresponding to previously sent electronic refill reminders;
generate a unique refill order number associated with the unique refill reminder identifier;
retrieve, using the unique refill reminder identifier, one or more prescription numbers associated with the unique refill reminder identifier, each prescription number corresponding to a previously filled prescription medication and a patient; and
transmit, over the communication network, a refill order confirmation electronic message to the customer, the refill order confirmation electronic message including refill order confirmation information for the one or more prescription medications.

18. The system of claim 17, wherein to retrieve the one or more prescription numbers corresponding to the one or more determined refill-eligible prescription medications for the customer, the instructions cause the server to:
retrieve a customer identifier associated with the customer;
generate the unique refill reminder identifier associated with the one or more retrieved prescription numbers and the retrieved customer identifier;
transmit, over the network, the electronic refill reminder to the customer, the electronic refill reminder including at least the generated unique refill reminder identifier and the customer identifier; and
validate the customer identifier by verifying that the customer identifier exists in a database of customer identifiers, the customer identifiers corresponding to customers that previously filled at least one prescription medication.

19. The system of claim 17, wherein to generate the refill order number, the instructions cause the server to:
verify whether a previously generated refill order number that is associated with the unique refill reminder identifier exists in a database of refill order numbers corresponding to previously filled orders; and
generate the refill order number only if no previously generated refill order number that is associated with the unique refill reminder identifier is found the database of refill order numbers.

20. The system of claim 17, wherein to validate the unique refill reminder identifier, the instructions cause the server to transmit, over the network, in response to the unique refill reminder identifier being invalid, an instructional electronic message that instructs the customer to reply to the electronic refill reminder again without modifying the refill reminder identifier.

* * * * *